US012745992B2

(12) United States Patent
Sigmon, Jr.

(10) Patent No.: US 12,745,992 B2
(45) Date of Patent: Sep. 29, 2026

(54) INTERNALLY BARBED BIOPSY STYLET AND SYSTEM

(71) Applicant: Cook Medical Technologies LLC, Bloomington, IN (US)

(72) Inventor: John Crowder Sigmon, Jr., Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 45 days.

(21) Appl. No.: 17/025,194

(22) Filed: Sep. 18, 2020

(65) Prior Publication Data

US 2021/0093307 A1 Apr. 1, 2021

Related U.S. Application Data

(60) Provisional application No. 62/907,926, filed on Sep. 30, 2019.

(51) Int. Cl.
*A61B 10/04* (2006.01)
*A61B 10/02* (2006.01)

(52) U.S. Cl.
CPC .......... *A61B 10/04* (2013.01); *A61B 10/0266* (2013.01); *A61B 2010/045* (2013.01)

(58) Field of Classification Search
CPC ................ A61B 10/04; A61B 10/0266; A61B 2010/045; A61B 10/06
See application file for complete search history.

(56) References Cited

U.S. PATENT DOCUMENTS 3,001,522 A * 9/1961 Silverman .......... A61B 10/0266 600/567
3,175,554 A * 3/1965 Stewart .............. A61B 10/0266 D24/147
3,404,677 A * 10/1968 Springer ................ A61B 17/29 606/174
3,929,123 A 12/1975 Jamshidi
5,074,311 A * 12/1991 Hasson .................. A61B 10/06 600/568
5,462,062 A * 10/1995 Rubinstein ........... A61B 10/025 604/272
5,649,547 A * 7/1997 Ritchart ............. A61B 10/0266 600/566

(Continued)

FOREIGN PATENT DOCUMENTS

FR 2 828 088 8/2001
WO 2004/000126 A1 12/2003

(Continued)

OTHER PUBLICATIONS

Extended EU Search Report for EP 20 19 7292, dated Feb. 19, 2021, 8 pp.

(Continued)

*Primary Examiner* — Rene T Towa
(74) *Attorney, Agent, or Firm* — Crowell & Moring LLP

(57) ABSTRACT

A tissue-collection stylet is configured with inward-facing barbs, for use in a needle, and particularly configured to capture intact tissue cores suitable for histological analysis. The stylet may be provided together with a needle as part of a biopsy system in which the stylet remains at least partially or fully within a lumen of the needle during collection of tissue samples and/or other samples.

15 Claims, 4 Drawing Sheets

(56) References Cited

U.S. PATENT DOCUMENTS

| | | | | | |
|---|---|---|---|---|---|
| 5,910,121 | A * | 6/1999 | Paolo | A61B 10/025 | 600/564 |
| 5,951,488 | A * | 9/1999 | Slater | A61B 10/0266 | 600/564 |
| 2004/0054377 | A1* | 3/2004 | Foster | A61B 17/221 | 606/167 |
| 2007/0027464 | A1* | 2/2007 | Way | A61B 17/1671 | 606/170 |
| 2007/0055263 | A1 | 3/2007 | Way et al. | | |
| 2007/0123890 | A1* | 5/2007 | Way | A61B 17/320016 | 606/79 |
| 2008/0045858 | A1* | 2/2008 | Tessitore | A61B 10/025 | 600/567 |
| 2008/0103504 | A1 | 5/2008 | Schmitz et al. | | |
| 2009/0287114 | A1* | 11/2009 | Lee | A61B 10/0266 | 600/564 |
| 2010/0076343 | A1* | 3/2010 | Vetter | A61B 90/39 | 600/567 |
| 2010/0317996 | A1* | 12/2010 | Dillon | A61B 10/0266 | 600/567 |
| 2012/0209140 | A1 | 8/2012 | Ryan | | |
| 2014/0163418 | A1* | 6/2014 | Gigi | A61B 10/0266 | 600/567 |
| 2019/0021706 | A1 | 1/2019 | Yori | | |
| 2019/0336124 | A1* | 11/2019 | Pisarnwongs | A61B 17/0482 | |

FOREIGN PATENT DOCUMENTS

| | | | | |
|---|---|---|---|---|
| WO | 2009/137288 A2 | 11/2009 | | |
| WO | WO-2017164277 A1 * | 9/2017 | | A61B 10/0096 |

OTHER PUBLICATIONS

Examination Report for European Application No. EP 20197292.4, dated Mar. 10, 2023, 3 pages.

International Search Report and Written Opinion for PCT/US2010/037002, dated Aug. 11, 2010, 9 pp.

* cited by examiner

INTERNALLY BARBED BIOPSY STYLET AND SYSTEM

CROSS-REFERENCE TO RELATED APPLICATIONS

This application claims priority to U.S. Provisional Application Ser. No. 62/907,926, filed Sep. 30, 2019, which is incorporated herein by reference in its entirety.

TECHNICAL FIELD

The invention relates generally to endoscopic surgical devices. More particularly, the invention pertains to a stylet for a needle where the stylet configured for biopsy collection during minimally-invasive procedures such as endoscopic procedures.

BACKGROUND

Biopsy of tissue from a patient can be an important means of obtaining diagnosis of a disease condition. Minimally invasive surgical methods of obtaining biopsied tissue samples have been developed that may lessen the discomfort a patient suffers during a biopsy procedure, and that often reduces the risk of infection by minimizing or eliminating punctures or incisions in the patient's external integument. Endoscopic methods such as those using gastro-esophageal endoscopy may use fine-needle aspiration (FNA) to obtain cell and/or tissue samples (where a sample that is larger may maintain more integrity between the cells therein). As used herein, "sample(s)" includes both cell samples and tissue samples, unless specified otherwise. When obtaining a sample by FNA, it is often necessary to pass the needle several times into/through the target site (e.g., tumor) in order to get a sufficient sample for diagnostic purposes. This repetitive process may lengthen the time of the procedure, introducing inefficiencies for the patient and attending medical personnel, and it may increase the discomfort suffered by a patient during the procedure. The process of several passes can include "fanning" where the needle is extended and retracted several times with its distal tip roughly defining an arc over the course of those reciprocal motions, and/or multi-pass procedures can include full retraction of a needle from the site, and later reintroduction of the same or different needle.

Fine needle aspiration (FNA) is a diagnostic biopsy procedure used to obtain a sample from a target site in a patient body. A fine needle (e.g., 19-gauge to 25-gauge) is directed to a target site, and suction is applied to a lumen of the needle to aspirate cells through its distal end, where the suction can be generated from the proximal end of the needle (e.g., by a syringe or other vacuum source) and/or by other means applied within and/or along the needle. The procedure typically is far less invasive than other biopsy techniques, whether performed percutaneously (e.g., to sample a suspected breast tumor or subcutaneous lesion) or endoscopically (e.g., to sample a suspected cholangiocarcinoma via a duodenoscope). Moreover, advances in endoscopic ultrasound (EUS) technology have helped physicians and patients by providing enhanced ability of a physician to visualize a biopsy needle to obtain a sample of material from a target site without requiring an open incision or use of large-bore needles and/or laparoscopic trocars.

Current FNA techniques typically obtain only a small number of cells useful for diagnostic evaluation. As a result, this technique includes a risk of false negatives where the few cells obtained in a sample do not accurately represent the presence of a tumor or other disease condition. The small sample size may also limit the diagnostic value of the procedure if the cells obtained are sufficiently few in number or sufficiently damaged during collection that they do not enable a definitive diagnosis. In the past decade, needles have been developed that are useful for EUS and/or percutaneous FNB (fine needle biopsy), which can obtain a larger sample size (e.g., a larger number of cells in the sample or a "core" comprising intact adjacent cells held together in similar form to their native location). However, there still exists a need in the field of biopsy—particularly as useful for rapid analysis—devices and methods that do not require a larger-gauge needle nor multiple passes of the needle to reliably obtain a diagnostically efficacious sample with regard to the number and integrity of the cells in the sample.

Many of the needles that are currently available for use during EUS endoscopy and other endoscopy procedures to collect tissue from and in the region of the pancreas, liver, and biliary tree often provide only disaggregated cells that are useful for cytological analysis. Such samples can be used for ROSE (Rapid OnSite Evaluation) where a cytopathologist can evaluate samples immediately, while in the surgical suite with the patient and the endoscopist/physician; however, most medical facilities do not have the resources to provide this, and it is quite expensive. As result, the physician typically must make multiple sampling passes in the patient's body, introducing/retracting/re-introducing the needle via an endoscope in order to get enough samples to have enough for a good probability of an accurate diagnosis upon cytopathology evaluation, which must be completed in a different time/place. Further, certain indications require or very strongly prefer histological examination for accurate diagnosis. For example, accurate diagnosis of auto-immune pancreatitis, lymphoma, submucosal tumors, and neuroendocrine tumors relies intact histological-grade samples, by which is meant intact tissue cores that preserve intact cells together with the material between the cells and maintaining aggregate structure that suitable for histological staining used, for example, in medical diagnostics in contrast with the disaggregated cells commonly obtained through FNA

DESCRIPTION

As used herein, the term "proximal" refers to the handle-end of a device held by a user, and the term "distal" refers to the opposite end. The term "surgical visualization device" refers to endoscopes including CCD, ultrasound, fiber optic, and CMOS devices, as well as other devices used for visualizing an internal portion of a patient body such as, for example, gastric endoscope (including duodenoscope), a laparoscope, or a bronchoscope. The terms "major" and/or "majority" refer to some portion greater than one half, while "minor" and/or "minority" refer to some portion less than one half. A typical stylet is essentially just a wire that occupies some or all of the cross-sectional.

Accordingly it is desirable to provide an endoscopically-usable device that is useful for collecting samples that can immediately be determined by visual review, of a physician in the operating suite, to contain intact tissue cores (a process called MOSE: Macroscopic On-Site Evaluation). These cores may be accompanied by cytological-analysis-quality materials, so that on-site cytology and histology evaluations are both available. Intact, histological-quality tissue samples (whether cores or other-shaped "chunks" of intact tissue may be fixed with a formalin solution and mounted in a paraffin block for slicing and staining (e.g., with immunohistochemical stains). This process may include forming "cell blocks" by standard pathology procedures that are similar to those used for "pinch biopsy" samples and for samples obtained when using larger needles (e.g., 19 gauge or larger, and also including percutaneous biopsy needles). The presently disclosed stylet provides for meeting these needs.

BRIEF SUMMARY

Embodiments disclosed here address these problems of the current technology and present advantages over existing needles with regard to both structure and methods. In one aspect, a method for obtaining a biopsy sample of histological-grade tissue includes steps of: directing a distal end of a needle to adjacent a target site, where the needle includes a needle lumen that is substantially completely or completely occupied by a first stylet; removing the first stylet from the needle lumen, and directing through the needle lumen a distal end of a second stylet, where the second stylet comprises: an elongate stylet body configured to pass through and occupy substantially the entire lengthwise needle lumen, the stylet body having a stylet body length extending from a proximal stylet end to a distal stylet end; a distal lengthwise portion of the stylet body including at least one longitudinal split forming at least two opposed legs, each leg having an inward-facing surface and an outward-facing surface; and an inward-facing surface of at least one of the legs comprising a plurality of barbs; and directing the distal end of the needle, occupied by the distal lengthwise portion of the stylet body, into the target site. In another aspect, A medical biopsy stylet includes an elongate stylet body configured to pass through and occupy substantially an entire lengthwise needle lumen, the stylet body extending from a proximal stylet end to a distal stylet end; a distal lengthwise portion of the stylet body including at least one longitudinal split forming at least two opposed legs, each leg having an inward-facing surface and an outward-facing surface; and an inward-facing surface of at least one of the legs comprising a plurality of barbs. In another aspect, a medical biopsy stylet and needle system includes an elongate needle including a needle lumen with a proximal lumen end, a distal lumen end, and lumen length therebetween; an elongate stylet body configured to pass through and occupy substantially the entire lengthwise needle lumen, the stylet body having a stylet body length extending from a proximal stylet end to a distal stylet end; a distal lengthwise portion of the stylet body including at least one longitudinal split forming at least two opposed legs, each leg having an inward-facing surface and an outward-facing surface; and an inward-facing surface of at least one of the legs comprising a plurality of barbs.

BRIEF DESCRIPTION OF THE DRAWINGS

In order to assist the understanding of embodiments of the invention, reference will now be made to the appended drawings, which are not necessarily drawn to scale or proportion (although some drawings may be drawn to scale as referenced below), and in which like reference numerals generally refer to like elements. The drawings are exemplary only, and should not be construed as limiting the invention.

FIG. 1A shows a top perspective view of a needle with split-end stylet, FIG. 1B shows a top perspective view of a split-end stylet; FIG. 1C shows a side elevation view of the needle and stylet; FIG. 1D shows a side elevation of the split-end stylet; and FIG. 1E shows a side elevation view of an alternative embodiment of the stylet end;

DETAILED DESCRIPTION

As used herein, the term "proximal" refers to the handle-end of a device held by a user, and the term "distal" refers to the opposite end. The term "surgical visualization device" refers to endoscopes including CCD, ultrasound, fiber optic, and CMOS devices, as well as other devices used for visualizing an internal portion of a patient body such as, for example, gastric endoscope (including duodenoscope), a laparoscope, or a bronchoscope. A typical stylet is essentially just a wire that occupies some or all of the cross-sectional area and volume and the lumen of a needle, where it provides, for example, columnar structural support and prevention of inadvertent/premature collection of material into the needle lumen (by the stylet occupying/blocking opening(s) and the internal volume of the needle lumen). The present stylet differs by providing an active role in engaging and harvesting tissue, in a different manner than prior stylets, some of which include one or more side apertures or cavities to interact with a side or end aperture of a needle where the stylet is moved in/out of the needle in a manner where opposed stylet surfaces and needle surfaces excise and capture a sample as a result of the relative movement of stylet and needle. In contrast, the present system does not require movement of the stylet relative to the needle to capture a sample, including that the present system includes preferred embodiments where the stylet is not moved relative to the needle during an operation to collect sample(s), including that the stylet does not extend out of the needle by much if at all while the needle is directed into a target site.

Figure 1A:
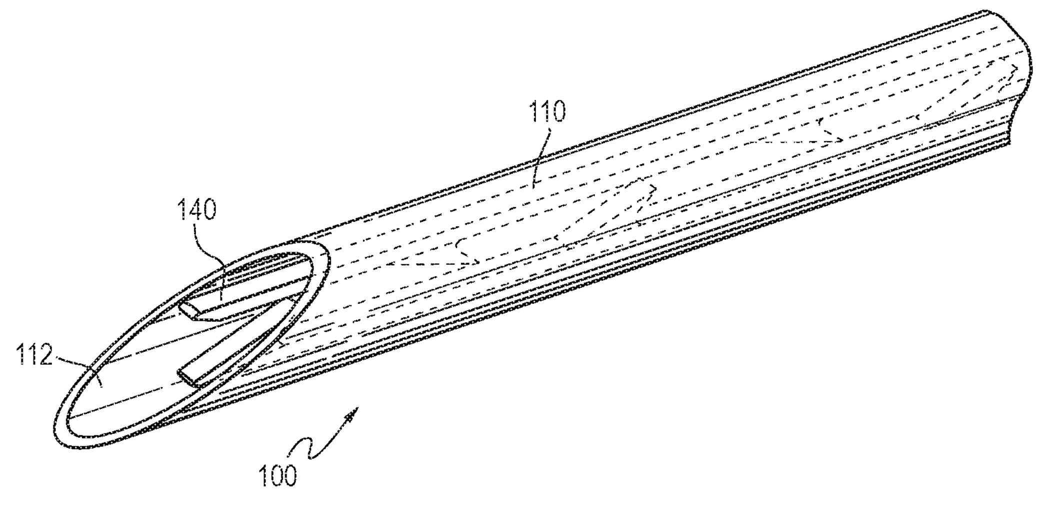
FIGS. 1A-1E show different views of a tissue-sampling needle and stylet embodiment, where

One embodiment of a tissue-sampling medical biopsy stylet, which may be part of a needle and stylet system 100, is described with reference to FIGS. 1A-1D, which show a tissue-sampling stylet 140. FIG. 1A shows the stylet 140 disposed within the needle lumen 112 of a needle 110. In this and many embodiments, the stylet 140 occupies a distalmost end length of the needle lumen 112, but the stylet does not extend much if any outside of the needle lumen during operation of the system to collect samples. This may be facilitated by a proximal stop or spacer element between a proximal stylet end and a proximal needle end (not shown in FIGS. 1A-1D, but known in the art and readily understandable by those of skill in the art in a variety of different configurations), configured to be removed to allow extension of the stylet through and out of the needle lumen's distal end, e.g., for releasing intact samples when collection is completed if the user wishes to withdraw the needle together with the stylet therein.

Figure 1B:
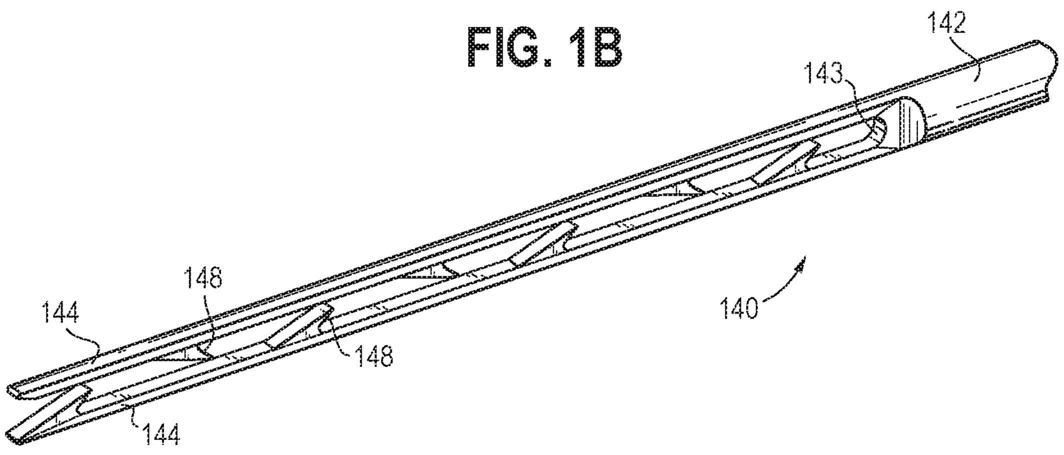
Figure 1C:
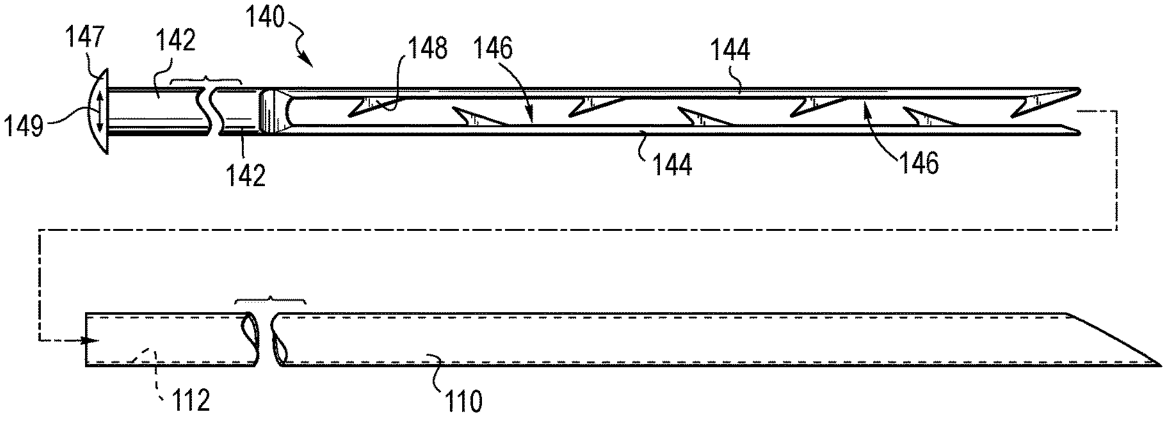
Figure 1D:
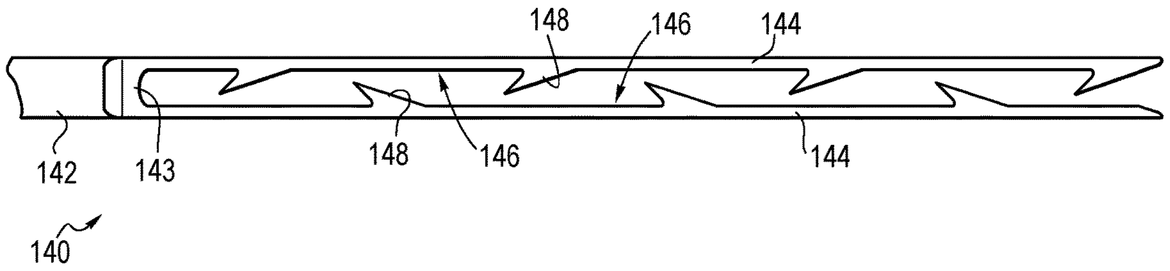

As shown in the side elevation view of FIGS. 1C and 1D, and the bottom perspective view of FIG. 1B, the stylet 140 includes an elongate stylet body 142 from which at least two legs 144 extend distally as part of a distalmost lengthwise portion of the stylet. The legs 144 meet proximally at a junction 143 with a proximal length of the body 142, where the length of the legs and the split is defined from this junction to the distal terminal end of the stylet body 142. Three or more legs may be used in other embodiments. The body 142 may include a circular and/or non-circular cross-section along a majority length or the entire length thereof (where, if for the entire length, the cross-sectional boundary will be interrupted by the split between the two or more legs). For example, as illustrated, the body is a solid cylinder with a circular cross-section, but those of skill in the art will readily appreciate and envision that the external surface of the body could be configured with a round but non-circular shape such as an ellipse or any other rounded shape, a cornered geometric shape (e.g., octagonal, decagonal, etc.), and/or could include one or more channels or other regular or irregular surface features along its length and/or around its outer circumference. The proximal length of the stylet body 142 may be solid in cross-section, as shown, and/or it may include one or more internal lumens or other structures.

In this embodiment, opposed inward-facing surfaces 146 of the legs 144 include regularly alternating opposed barbs 148. The barbs 148 in this embodiment include a generally wedge shape as viewed in longitudinal section. FIG. 1D is illustrated to scale (+/−0.004 inches) with the stylet 140 being dimensioned for occupying the lumen of a 19 gauge endoscopic needle, including an outer diameter of 0.30 inches (where the specific measurements are provided by way of non-limiting example of one embodiment that performed well in experiments with mammalian tissue, while the proportions and exact measurements in other embodiments may vary significantly from the numbers presented here, although those of skill in the art will be enabled by the present disclosure to practice a split-stylet and needle system for biopsy using inward-facing barbs on stylet legs, within the scope of this disclosure). The legs extend about 0.531 inches from a midpoint of the juncture region 143 to the distal end terminus of the stylet 140. The juncture 143 between the legs includes a 0.009 inch radius connecting the opposed inner leg surfaces 146. The juncture 143 also includes a transition region between the cylindrical cross-section of the proximal length of the body 142 and the generally rectangular cross-section defined by and space between the legs.

Each leg 144 is 0.005 inches thick between the barbs 148, and each barb 148 extends inwardly from the inner leg surface 146 by a perpendicular distance of 0.004 inches, leaving a gap of 0.006 inches between a tip of the barb 148 and the opposite inner leg surface 146. The major proximal-facing surface of each barb 148 is disposed at an angle of 40° relative to the inward-facing leg surface 146 with a minor proximal face radiused at 0.003 inches to transition to the inner leg surface 146. As such, each barb 148 extends across a central longitudinal axis of the space between the legs 144, which—in this embodiment—is the same central longitudinal axis of the entire illustrated portion of the stylet 140. In other embodiments the angle will be greater than 0° and less than or equal to 90°, generally from about 20° to about 70°, and with some embodiments from about 35° to about 55°, with other ranges and/or specific angles being within the scope of this disclosure, and subject also to the type of tissue sample being targeted. The distance between the proximal end of one barb on the inner surface 146 and the distal end of the next proximally-adjacent barb is 0.117 inches, and the height of each barb from the inner surface is 0.014 inches. The distalmost terminus of each of the legs angled to form a bevel with the outermost diametric surface of each leg, as illustrated. The distalmost barb has a complete length of 0.044 inches along the longitudinal axis, measured from the distalmost terminal end of the leg on which that barb is disposed. The next-distalmost barb, on the opposite leg, is disposed 0.071 inches from the distalmost terminal end of the leg on which that barb is disposed to the proximal end of the barb where its distal surface angles upward/away from the inner surface of that leg.

As shown in FIG. 1B, the legs 144 may each have a generally rectangular or square cross-section, except that the outermost surface may include the outer circumferential curve of the rest of the generally cylindrical stylet body 142. In this embodiment, the barbs are generally wedge-shaped, but other embodiments may have different barb geometries. In certain embodiments, the longitudinal split between the legs is from about 0.5% to about 2% of the entire length of the stylet (for example, with some standard stylet lengths such as a 180 cm stylet, this may be at least about 10 mm/about 0.4 inches). In many diagnostic procedures, a desirable tissue core may be about 15 mm in length, while a longer core may also be desirable and a shorter core may be acceptable, such that a split length generally will be greater than about 5 mm, and may be 30 mm or greater, where such split length may be somewhat discontinuous by including one or more reinforcing members between the legs as described elsewhere in the present disclosure. FIG. 1C also indicates the introduction of the stylet 140 into and through the lumen 112 of the needle 110. The needle 110 is shown in a simplified manner without the handle, sheath, and/or other structures that are well-known in the art for different needle embodiments, and those of skill in the art will appreciate that various embodiments of the present system may use different handle and/or sheath configurations already in use or to be developed for endoscopic, laparoscopic, percutaneous, and/or other applications of the present system.

In the embodiment illustrated in FIGS. 1A-1D, the barbs 148 are evenly staggered/alternated in an opposing manner along the inward-facing stylet leg surface 146. In other embodiments, the barbs may be directly or partially opposed, and/or they may be staggered in a regularly or irregularly spaced manner—including variations of these and other configuration in a single embodiment and/or in different embodiments. Also, the barbs shown are all oriented the same way and are substantially the same as each other. However, in other embodiments, one or more barbs may be shaped differently from other barbs, and they may be oriented at different angles relative to each other and/or to a longitudinal central axis defined by the stylet and/or needle. Certain embodiments include at least some of the barbs being oriented in a manner that the lowest-profile end of the barb is more distal and the highest/largest-profile end of the barb is more proximal, which is true of the embodiment shown in FIGS. 1A-1D. In most embodiments, at least one of the plurality of barbs includes a pointed surface, an angled surface, or both, where each barb is disposed at an angle of 90 degrees or less relative to a portion of the inward facing surface proximal of that barb, which may be between 30 degrees and 50 degrees.

Different needle embodiments may be practiced within the scope of the present disclosure. For example, the needle configuration described above includes non-limiting exemplary dimensions for one embodiment of an endoscopic 19 gauge needle, which will have sufficient length and flexibility to access target sites including the biliary ducts, liver, pancreas, small or large intestine, or in any tissue or organ adjacent to the gastrointestinal tract of a patient through a working channel of a duodenoscope or an end-viewing gastrointestinal endoscope. Other embodiments of a stylet and/or of a stylet and needle system may be configured for endoscopic, laparoscopic, percutaneous, and/or other access to those or other organs such as lungs, small intestine, large intestine, testes, uterus, ovaries, or any other body structure, where these and other embodiments may include different proportions and different absolute measurements of one or more elements. In some embodiments, the needle and/or the stylet may include echogenicity-enhancing features of any type known in the art including surface ridges, dimples, and/or protrusions, inclusions and/or vacant spaces within the otherwise solid portions, and/or any other echogenicity-enhancing features known or developed in the art. Even without enhancement, the structure described and illustrated will present an echogenically-visualizable profile. In some embodiments, the needle and stylet can be configured as rigid—or at least less flexible than—endoscopy needles, particularly for percutaneous use (e.g., for gastrointestinal use, for use in obtaining biopsy samples from breast, prostate, and/or other organs/structures).

Figure 2A:
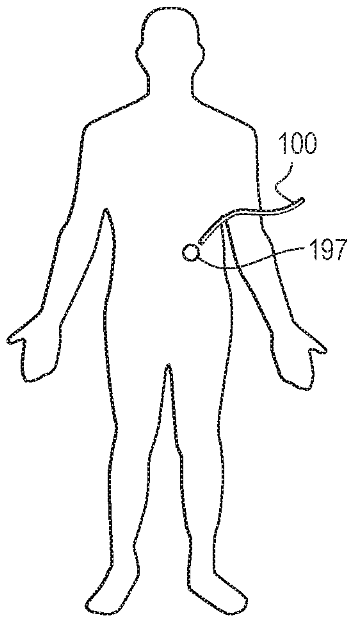
FIGS. 2A-2C show diagrammatically a method of using the needle and stylet system.
Figure 2B:
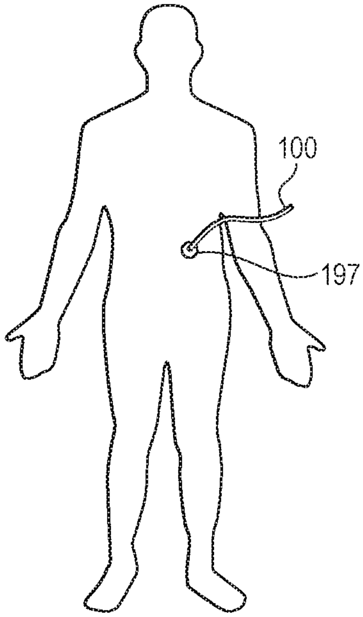
Figure 2C:
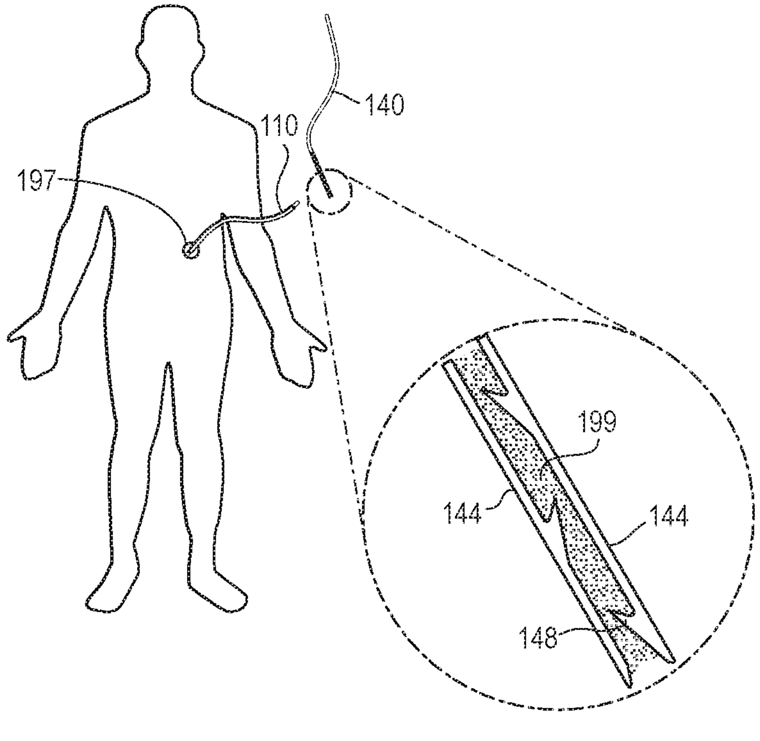

In operation, the present system can present advantages over the known art. As diagrammatically described with reference to FIGS. 2A-2C (not to scale) and the structures of FIGS. 1A-1D, in one method, the distal end portion of a needle and stylet system 100 is directed to a target site 197 (FIG. 2A). The target site may be visualized using endoscopy, fluoroscopy, and/or any other visualization technique (including, for example, video visualization of an endoscope), including during directing the system 100 to that site. The distal end portion of a needle and stylet system 100 is directed into a target site 197 in a manner with the needle 110 penetrating tissue of the target site and receiving tissue 199 into the needle lumen 112 where barbs 148 of the stylet legs 144 engage into the tissue (FIG. 2B). The distal end of the needle 110 may be left in place and the stylet 140 withdrawn from the needle lumen 112, including with the barb-captured sample (FIG. 2C including magnified detail of legs 144 with intact tissue sample 199).

A user or other person can conduct a quick inspection (with or without dye(s), magnification, and/or other means) to determine if the captured sample is sufficient to provide desired diagnostic information. If another sample is desired, the stylet 140 can be reintroduced into the needle lumen 112 and directed all the way to its original position with the barbed legs in the distal end. Before, during, or after this reintroduction, the needle position can be adjusted to engage a different portion of the target region (cf. FIG. 2B), and the process of sample capture, withdrawing the stylet, and inspecting the captured sample can be repeated without removing the entire needle (see FIG. 2C). This process provides for less time and fewer needle-penetrations than many prior needle biopsy systems while maintaining needle position in a target region until a desirable sample is obtained. For many diagnostic purposes, a desirable sample may include tissue with intact adjacent cells and the material around and between the cells that will provide for histological analysis as well as cytological analysis and/or other analytical techniques. In another method embodiment, a standard solid-body stylet (not shown here, but very well known in the art as standard for endoscopic needles) may occupy the needle lumen 112 during introduction until the distal end of the needle 110 is immediately adjacent to—or even within—the target region to be sampled (e.g., as shown in FIG. 2A). Then, that solid stylet can be withdrawn and a split-end stylet (e.g., 140) directed through the needle lumen 112, at which time the system 100 is advanced into the target site in a manner that tissue will be engaged between and captured by the legs 144. This method step using a solid stylet will decrease the likelihood of inadvertently capturing matter in the split region before a user wishes to do so.

The needle 100 may be an 18 gauge or smaller needle (e.g., 19 gauge, 22 gauge, 25 gauge, etc.). In one 19 gauge needle embodiment, the longitudinal split between the at least two legs of the stylet extends about 0.5 inches along a longitudinal axis of the stylet. At least one of the barbs includes a proximal barb surface disposed at an angle of about 40 degrees to a portion of the inward-facing surface proximal of said barb. The at least two opposed legs are about 0.5 inches in length and about 0.005 inches thick. A gap between a majority length of the inward-facing surfaces of the legs is about 0.008 inches. At least one of the barbs extends out from the inward-facing surface by about 0.006 inches and has a total longitudinal length of about 0.044 inches, and as measured along the inward facing surface, adjacent barbs are separated by about 0.117 inches. In most preferred embodiments, the stylet is configured to retain a biopsy sample of histological-grade tissue suitable for providing a user with intact tissue that is useful for diagnostic purposes using histology and/or other techniques that analyze aggregate tissue in or near its native configuration with adjacent cells still aggregated together with related and intervening material.

Figure 1E:
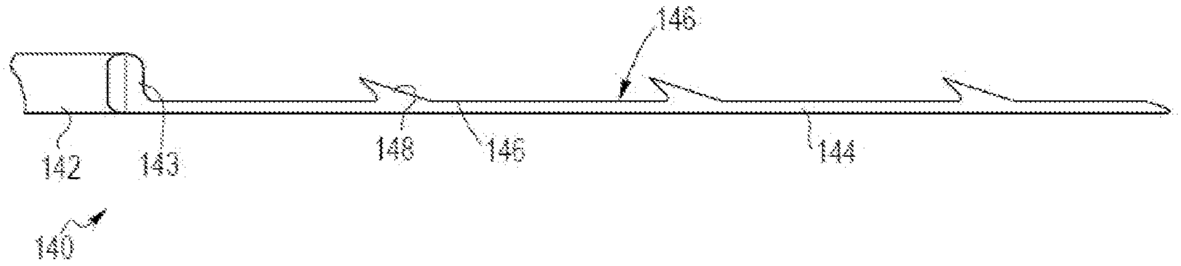
Figure 3:
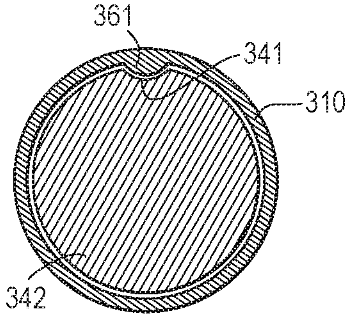
FIG. 3 shows another tissue-sampling needle and stylet embodiment in transverse section view.
Figure 4:
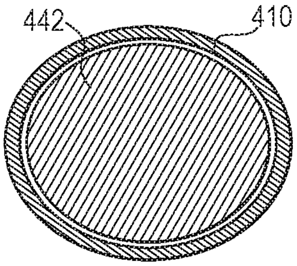
FIG. 4 shows another tissue-sampling needle and stylet embodiment in transverse section view.

As shown in FIG. 1C, in some embodiments, a proximal stylet cap 147 or other proximal structure may be provided, which may include visual indicia such as marking 149 to indicate the rotational orientation of the legs 144 for a user. As shown in FIG. 3, a needle 310 may also include an inward/lumen-facing structure 361 that engages a complementarily shaped structure 341 of a stylet body 342 in a manner preventing relative rotation of the engaged lengthwise portions of the needle and the stylet body. As shown in FIG. 4, some embodiments may include the stylet body length 442 proximal of the stylet legs having a lengthwise portion with a non-circular cross-section 451 of a needle 410 and stylet 440. Each of FIGS. 3 and 4 represent a section view taken across a needle and solid body portion of the stylet within the needle, which will be understood by those of skill in the art without an external side view representation of the needle and stylet (that would otherwise look like FIG. 1A). Although each of the embodiments illustrated include two legs as a split stylet, it should be appreciated that any of the embodiments may be provided with a single leg by omitting one of the legs 144 therefrom, which is readily understandable from the text and illustrations herein, including FIG. 1E, which is presented by way of non-limiting example, although the opposite leg may be the single-leg and—as in other embodiments—may have more or fewer barbs 148 in different locations. Such a single-leg embodiment may present certain other advantages including larger sample size captured within the needle lumen space adjacent to the single leg.

Figure 5:
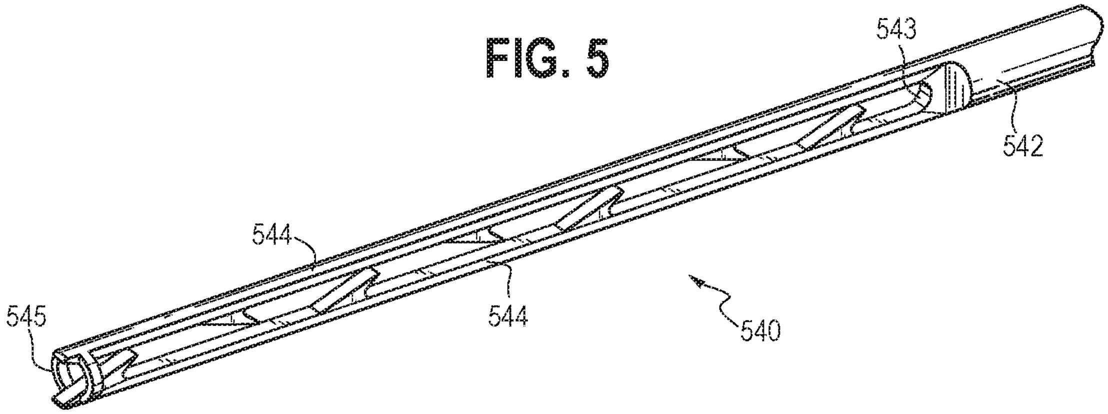
FIG. 5, which shows a different embodiment of a stylet end.

In some embodiments one or more reinforcing structures connecting the legs together may be included, where one example of such a structure is shown as an intact ring 545 in FIG. 5, which shows a different embodiment of a stylet end for use within the presently disclosed systems and methods. In this drawing, the stylet 540 includes an elongate stylet body 542 from which at least two legs 544 extend distally as part of a distalmost lengthwise portion of the stylet. The legs 544 meet proximally at a junction 543 with a proximal length of the body 542. And, the legs 544 are connected nearer the distal end by an intact wall 545 that is ring-shaped in this embodiment, but which—in other embodiments—can be shaped in any other manner that will provide increased structural support at any point(s) along the legs 544 while not significantly impeding functionality of the legs and barbs 548 for engaging and harvesting intact tissue samples. The illustrated ring 545 has a blunt leading edge, but other embodiments may be rounded, chamfered, beveled, and/or provided with other shaping that may provide one or more of structural strength, insertion/removal force change, altered contact with needle lumen surface, or other features or functions.

The needle and stylet device and methods disclosed here provide the advantages associated with FNA needles of small size and maneuverability, while offering a means of collecting more intact FNB samples from target sites. They also are not hampered by the guillotine-style moving parts of notched needle systems and other stylet-plus-needle systems that collect tissue by using opposed cutting or shearing surfaces known in the biopsy art (which often are larger in scale due to a need for having a cutting member that movably transects a notch or aperture of needle and/or stylet).

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

I claim:

1. A medical biopsy stylet and needle system, comprising:

an elongate needle including a needle lumen with a proximal lumen end, a distal lumen end, and lumen length therebetween;

an elongate stylet body configured to pass through and occupy substantially the entire lengthwise needle lumen, the stylet body having a stylet body length extending from a proximal stylet end to a distal stylet end, where the stylet body length is substantially the same as a needle lumen length such that the stylet does not extend past a distal needle terminus;

a single leg of a distal lengthwise portion of the stylet body having an inward-facing surface and an outward-facing surface; and the inward-facing surface of the single leg comprising a plurality of barbs, configured to collect intact tissue, where the stylet body extending between the distal lengthwise portion of the stylet and the proximal stylet end includes a solid cross-section.

2. The system of claim 1, where one or more individual barbs of the plurality of barbs is shaped differently from one or more other individual barbs of the plurality of barbs.

3. The system of claim 1, further comprising a stylet handle disposed on the proximal end of the stylet body.

4. The system of claim 1, where the stylet body proximal of the single leg includes a lengthwise portion with a circular cross-section, a lengthwise portion with a non-circular cross-section, or both.

5. The system of claim 4, where the stylet body proximal of the single leg includes a lengthwise portion with a non-circular cross-section, and the needle lumen includes a complementarily shaped inward-facing structure that engages the stylet body in a manner preventing relative rotation of the engaged lengthwise portions of the needle and the stylet body.

6. The system of claim 5, further comprising visual indicia of the rotational orientation of the leg relative to the needle.

7. The system of claim 1, where the needle is a 19 gauge needle or smaller and is configured with sufficient length and flexibility to operate through an endoscope to a target site in a patient body, said target site being selected from in a lung location, in a liver location, in a pancreas location, in a small intestine location, and in a large intestine location.

8. A medical biopsy stylet and needle system, comprising:

an elongate needle including a needle lumen with a proximal lumen end, a distal lumen end, and lumen length therebetween;

an elongate stylet body configured to pass through and occupy substantially the entire lengthwise needle lumen, the stylet body having a stylet body length extending from a proximal stylet end to a distal stylet end, where the stylet body length is substantially the same as a needle lumen length such that the stylet does not extend past a distal needle terminus;

a distal lengthwise portion of the stylet body including at least one leg having an inward-facing surface and an outward-facing surface; and the inward-facing surface of at least one of the legs comprising a plurality of barbs, configured to collect intact tissue without rotation, where the stylet body extending between the distal lengthwise portion of the stylet and the proximal stylet end includes a solid cross-section, configured such that the biopsy stylet is not moved relative to the needle lumen during collection.

9. A medical biopsy stylet and needle system, comprising:

an elongate needle including a needle lumen with a proximal lumen end, a distal lumen end, and lumen length therebetween;

an elongate stylet body configured to pass through and occupy substantially the entire lengthwise needle lumen, the stylet body having a stylet body length extending from a proximal stylet end to a distal stylet end, where the stylet body length is substantially the same as a needle lumen length such that the stylet does not extend past a distal needle terminus, including during a tissue-collection operation;

a distal lengthwise portion of the stylet body including at least one leg having an inward-facing surface and an outward-facing surface; and the inward-facing surface of at least one of the legs comprising a plurality of barbs, configured to collect intact tissue without rotation, where the stylet body extending between the distal lengthwise portion of the stylet and the proximal stylet end includes a solid cross-section, and the solid cross-section includes a keyseat that engages with a complimentarily shaped inward-facing structure of the needle lumen.

10. The system of claim 9, where one or more individual barbs of the plurality of barbs is shaped differently from one or more other individual barbs of the plurality of barbs.

11. The system of claim 9, further comprising a stylet handle disposed on the proximal end of the stylet body.

12. The system of claim 9, where the stylet body proximal of the legs includes a lengthwise portion with a circular cross-section, a lengthwise portion with a non-circular cross-section, or both.

13. The system of claim 12, where the stylet body proximal of the legs includes a lengthwise portion with a non-circular cross-section, and the complementarily shaped inward-facing structure of the needle lumen engages the stylet body in a manner preventing relative rotation of the engaged lengthwise portions of the needle and the stylet body.

14. The system of claim 13, further comprising visual indicia of the rotational orientation of the leg relative to the needle.

15. The system of claim 9, where the needle is a 19 gauge needle or smaller and is configured with sufficient length and flexibility to operate through an endoscope to a target site in a patient body, said target site being selected from in a lung location, in a liver location, in a pancreas location, and in a small intestine location, and in a large intestine location.

* * * * *